United States Patent [19]

Dai

[11] 4,200,763

[45] Apr. 29, 1980

[54] BENZOIC ACID ESTER DERIVATIVE

[75] Inventor: Sheng-Hong A. Dai, Wallingford, Conn.

[73] Assignee: The Upjohn Company, Kalamazoo, Mich.

[21] Appl. No.: 38,257

[22] Filed: May 11, 1979

Related U.S. Application Data

[60] Division of Ser. No. 879,788, Feb. 21, 1978, Pat. No. 4,164,510, which is a continuation-in-part of Ser. No. 818,233, Jul. 22, 1977, abandoned.

[51] Int. Cl.$^2$ .............................................. C07C 69/78
[52] U.S. Cl. ................................................... 560/109
[58] Field of Search ........................................... 560/109

[56] References Cited

U.S. PATENT DOCUMENTS

| | | | |
|---|---|---|---|
| 2,773,906 | 12/1956 | Emerson | 260/610 B |
| 2,862,973 | 12/1958 | Winkler et al. | 260/610 B |
| 2,954,405 | 9/1960 | Hock et al. | 260/610 B |
| 3,028,410 | 4/1962 | Zimmer | 260/461 |
| 3,402,205 | 9/1968 | Gregory | 560/109 |
| 3,634,328 | 1/1972 | Brownstein | 260/610 B |
| 3,666,815 | 5/1972 | Scheltus | 260/610 B |

*Primary Examiner*—Paul J. Killos
*Attorney, Agent, or Firm*—James S. Rose; Denis A. Firth

[57] ABSTRACT

Isopropylphenyl esters are converted to di- or trihydric phenols via a novel autoxidation of the esters at high conversion rates to the corresponding hydroperoxyisopropylphenyl esters in the presence of a catalyst combination comprising at least two members selected from the group consisting of (i) a metal phthalocyanine; (ii) a di-tertiary alkyl peroxide; and (iii) a tertiary alkyl hydroperoxide.

Rearrangement of the hydroperoxyisopropylphenyl esters to the corresponding hydroxyphenyl esters and the hydrolysis of the latter compounds provides the phenols in overall yields (from the starting esters) heretofore not obtainable. Novel bis(hydroperoxyisopropylphenyl)carbonates are described which are attractive intermediates for the intermediate bisphenol carbonate or the final hydroquinone hydrolysis product.

1 Claim, No Drawings

BENZOIC ACID ESTER DERIVATIVE

CROSS-REFERENCE TO RELATED APPLICATION

This application is a division of application Ser. No. 879,788, filed Feb. 21, 1978, now U.S. Pat. No. 4,164,510, which in turn is a continuation-in-part of copending application, Ser. No. 818,233 filed July 22, 1977, now abandoned.

BACKGROUND OF THE INVENTION

1. Field of the Invention

This invention relates to the autoxidation of alkyl aromatic compounds and is more particularly concerned with an improved process for the preparation of hydroperoxyisopropylphenyl esters, including novel bis(hydroperoxyisopropylphenyl)carbonates and bis(hydroxyphenyl)carbonates produced therefrom, and further relates to an improved process for the preparation of di- and trihydric phenols via said hydroperoxyisopropylphenyl esters.

2. Description of the Prior Art

The autoxidation of cumene and cumene type hydrocarbons to cumene hydroperoxide and the like is a well known procedure; see, for example, U.S. Pat. Nos. 2,820,064, 2,954,405, 3,634,328, and 3,803,243. U.S. Pat. No. 3,666,815 discloses similar type oxidation procedures leading to alcohol products and U.S. Pat. No. 3,816,548 shows the catalytic oxidation of isoparaffin hydrocarbons to alcohols using techniques similar to those described for the aromatic compounds.

Kropf et al (Liebigs Ann. Chem. 1975, 2010–2022 and J. Prakt Chem. 9, 173–86, 1959) have disclosed the use of metal phthalocyanines as catalysts in oxidizing cumene type hydrocarbons to cumyl hydroperoxides.

When an oxygen substituent, as in the case of an isopropylphenyl ester, is attached to the aromatic ring the autoxidation of the isopropyl group to the α-cumyl hydroperoxide derivative is complicated by the formation of side products and yields or conversions tend to be lower. Generally speaking, this is attributed to the presence of trace amounts of phenolic impurities which can arise from the hydrolysis of the phenyl ester.

Hydroperoxides of difficulty saponifiable esters of isopropylphenols are prepared in the liquid state with an oxygen containing gas at a temperature of about 20° C. to about 125° C. in the presence of an antacid as shown in U.S. Pat. No. 2,799,695. Reaction times are very long, of the order of days, while conversions are low.

U.S. Pat. No. 2,799,698 discloses the oxidation of p-isopropylphenyl acetate directly to hydroquinone diacetate in the presence of acetic anhydride.

The autoxidation of difficultly hydrolyzable esters of α,α-dialkylmethylphenols is reported in U.S. Pat. No. 2,799,715 by contacting said esters with an oxygen gas at 20° C. to 125° C. in the presence of an antacid. The hydroperoxides so formed are converted to the corresponding dihydric phenols. As in the case of U.S. Pat. No. 2,799,695, the reaction times are very long with low conversions.

Zimmer (U.S. Pat. No. 3,028,410) discloses the autoxidation of various isopropylphenyl esters to hydroperoxide derivatives. Reaction conditions include high reaction temperatures of 140° C. to 160° C. which is considered to be a high range when working with organic peroxidic materials; mono or dihydroperoxides of isopropylaromatic compounds are disclosed as catalysts. Conversions are reported on the basis of total hydroperoxide content of the reaction mixture alone. U.S. Pat. No. 2,954,405 broadly discloses the use of combinations of metal phthalocyanines with hydroperoxides in the autoxidation of alkyl aromatic compounds.

The hydroperoxyisopropylphenyl esters disclosed in the art cited above serve as intermediates for the preparation of dihydric phenols by the acid catalyzed rearrangement of the hydroperoxyisopropyl compounds to the corresponding hydroxyphenyl esters and acetone and subsequent saponification of the hydroxyphenyl ester to the dihydric phenol; see U.S. Pat. No. 2,799,695, 2,799,715, and 3,028,410.

It has now been discovered that isopropylphenyl esters can be autoxidized with essentially no induction period at a much faster rate with a higher conversion and selectivity and higher isolated yield of desired hydroperoxide product than has hitherto been possible while operating at relatively low and safe temperatures. Furthermore, the more facile preparation of the hydroperoxyisopropylphenyl esters provides for an improved means for the preparation of di- or trihydric phenols in overall increased yields.

SUMMARY OF THE INVENTION

This invention comprises a process for the autoxidation of an isopropylphenyl ester to the hydroperoxyisopropylphenyl ester in the presence of oxygen wherein the improvement comprises carrying out said autoxidation at a temperature of from about 80° C. to about 130° C. in the presence of a catalyst combination comprising at least two members of the group consisting of (i) a metal phthalocyanine; (ii) a di-tertiary alkyl peroxide; and (iii) a tertiary alkyl hydroperoxide.

The invention also comprises an improved process for the preparation of di- or trihydric phenols.

The invention also comprises certain novel hydroperoxyisopropyl phenyl esters.

The term "isopropylphenyl ester" means a phenyl ester having the formula

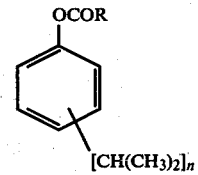

I wherein n equals 1 or 2 provided that when n equals 1 the isopropyl radical is substituted either in the meta or para position on the phenyl ring relative to the ester group and when n equals 2 the isopropyl radicals are substituted in each meta position, and wherein R is selected from the group consisting of alkyl from 1 to 8 carbon atoms, inclusive, aryl from 6 to 12 carbon atoms, inclusive, alkaryl from 7 to 14 carbon atoms inclusive, aralkyl from 7 to 14 carbon atoms, inclusive, and radicals having the formula

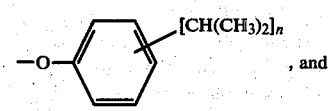

Ia

, and

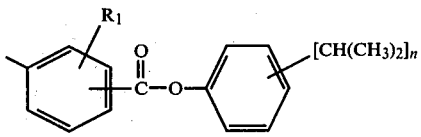

Ib wherein n is defined as above, R₁ is selected from the group consisting of hydrogen and alkyl from 1 to 4 carbon atoms, and the carbophenoxy substituent can be in the ortho, meta, or para position to the valency bond of the radical.

The term "hydroperoxyisopropylphenyl ester" means the autoxidation product derived from formula (I) wherein the tertiary isopropyl hydrogen atom has been replaced by the hydroperoxy radical and said hydroperoxyisopropylphenyl ester has the formula

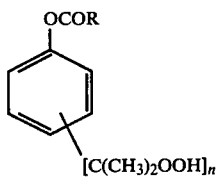

II wherein n and R are both defined as set forth above and further provided that when the radical R contains isopropyl radicals as in the case of Ia or Ib set forth above then said isopropyl radicals may also have their tertiary isopropyl hydrogen atoms replaced by the hydroperoxy radical.

The term "alkyl from 1 to 4 carbon atoms" means methyl, ethyl, propyl, butyl, and isomeric forms thereof.

The term "alkyl from 1 to 8 carbon atoms" means the alkyl groups set forth above as well as pentyl, hexyl, heptyl, octyl, and isomeric forms thereof.

The term "aryl from 6 to 12 carbon atoms" means phenyl, biphenyl, naphthyl, and the like.

The term "alkaryl from 7 to 14 carbon atoms" means tolyl, ethylphenyl, xylyl, 3,5-dimethyl-α-naphthyl, 3,5-diethyl-α-naphthyl, and the like.

The term "aralkyl from 7 to 14 carbon atoms" means benzyl, p-methylbenzyl, p-ethylbenzyl, β-phenylethyl, γ-phenylpropyl, δ-phenylbutyl, δ-(2,4-dimethylphenyl)butyl, δ-(2,4-diethylphenyl)butyl, and the like.

The term "tertiary alkyl hydroperoxide" means a hydroperoxide compound containing at least one hydroperoxide group wherein the oxygen is bonded to a tertiary carbon atom wherein at least two of the other groups bonded to said carbon atom are alkyl from 1 to 8 carbon atoms and the third group bonded to said carbon is selected from the class consisting of alkyl from 1 to 8 carbon atoms, cycloalkyl from 5 to 10 carbon atoms inclusive, and aryl from 6 to 12 carbon atoms inclusive. Illustrative of said tertiary alkyl hydroperoxides are t-butyl hydroperoxide, 1,1,3,3-tetramethylbutyl hydroperoxide, 2,5-dihydroperoxy-2,5-dimethylhexane, p-menthane hydroperoxide, cumene hydroperoxide, and 1,4-di(hydroperoxyisopropyl)benzene, and the like.

The term "di-tertiary alkyl peroxide" means a peroxidic compound containing at least one peroxy grouping wherein each oxygen atom is bonded to a tertiary carbon atom wherein the remaining groups attached to said carbon atom are the same as defined above. Illustrative of said di-tertiary alkyl peroxides are di-t-butyl peroxide, dicumyl peroxide, 2,5-dimethyl-2,5-di(t-butylperoxy)hexane, and the like.

DETAILED DESCRIPTION OF THE INVENTION

The process of the present invention can be used for the preparation of di- or trihydric phenols in accordance with the following reaction scheme.

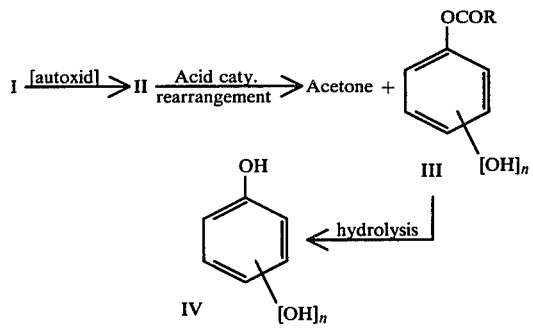

The isopropylphenyl ester (I) defined hereinabove is autoxidized by the novel process in accordance with the present invention to the hydroperoxyisopropylphenyl ester (II) also defined hereinabove. Acid catalyzed rearrangement of (II) gives rise to the formation of acetone and the formation of a phenolic hydroxyl function at the site originally occupied by the hydroperoxyisopropyl group to form (III). Simple acid or base catalyzed hydrolysis of the ester group of (III) gives rise to the formation of another phenolic hydroxyl group as illustrated in (IV).

The principal polyhydric phenols prepared in accordance with the present invention are those di- or trihydric phenols having the structure (IV). However, it will be obvious to one skilled in the art that other phenols having the formula (III) can also be prepared in accordance with the present invention wherein the ester group is left intact. The hydroxyl functionality of (III) will depend on the value of n and the nature of the radical R as defined hereinbefore, and can have a value from one to four inclusive.

A preferred isopropylphenyl ester to be used in accordance with the present invention has the formula (I) wherein n is defined as above and R is selected from the group consisting of alkyl, aryl, and the radical (Ia) all defined as above.

A most preferred isopropylphenyl ester has the formula

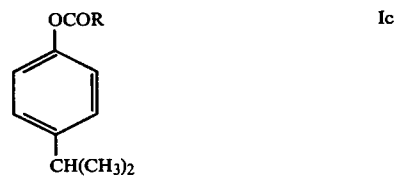

Ic wherein R is selected from the group consisting of alkyl, aryl, and the radical (Ia) wherein n=1 and the isopropyl group is in the para position, and alkyl and aryl are as defined above.

The improved process in accordance with the present invention for the autoxidation of an isopropylphenyl ester (I) to the hydroperoxyisopropylphenyl ester (II) is carried out conveniently by intimately mixing the isopropylphenyl ester with a moisture free gas rich in oxygen content, such as air, but, preferably oxygen, at a temperature of from about 80° C. to about 130° C., preferably from about 100° C. to about 120° C., in the presence of one of the catalyst combinations set forth above. The individual components (i), (ii), and (iii) can be paired in any order desired just so long as at least two are present in the combination during the autoxidation.

The progress of the autoxidation reaction can be studied using any convenient analytical technique. However, a particularly simple, rapid, yet accurate method comprises removing aliquots periodically from the reaction mixture and determining the proton nuclear magnetic resonance spectrum of the sample. A comparison of the integration area of proton resonance arising from the methyl groups of the hydroperoxyisopropyl group with the integration area of proton resonance derived from the methyl groups of the starting isopropyl group provides a rapid measure of the total mole percent conversion to hydroperoxide. From this data a rate of mole percent conversion can be determined.

While the autoxidation process in accordance with the present invention can be run to high molar percent conversions, for example in excess of 40 mole percent, it is preferred that the conversion not be allowed to exceed about 40 mole percent so that hydroperoxide product selectivity can be maximized to well above 90 percent. Otherwise, increased conversion leads to poorer selectivity. The starting material or incompletely oxidized material is simply recovered and recycled in subsequent autoxidations.

Yet another convenient means for analyzing the progress of the reaction, and, more particularly, the actual product selectivity or percentage concentration of each product formed which includes the side-products as well as the compound (II), is to analyze an aliquot by high pressure liquid chromatography (HPLC) (see Modern Practice of Liquid Chromatography edited by J.J. Kirkland, 1971, Wiley Intersciences, Div. of John Wiley & Sons, Inc., New York, N.Y.).

Using these analytical procedures in studying the autoxidation process of the present invention, rates of conversion have been observed (up to 40 mole percent in 3 hours) at levels of product selectivity (greater than 90 percent) which hitherto have not been obtainable with prior art methods.

Moreover, these analytical methods provide a simple means for determining when the autoxidation may be conveniently stopped. Generally speaking, the autoxidation is conducted over a period of time from about 1 hour to about 15 hours and preferably from about 2 hours to about 8 hours.

The t-alkyl hydroperoxide and di-t-alkyl peroxide components, whether employed together or separately, are each advantageously employed in the catalyst combination in an amount of from about 0.1 percent by weight to about 4 percent by weight of (I) and preferably from about 0.3 to about 2.0 percent.

The use of peroxy ester compounds such as dibenzoyl peroxide, stearoyl peroxide, and the like are specifically excluded because the use of such compounds is deleterious due to the trace amounts of acidic impurities which cause trace hydrolysis to occur at the phenyl ester groups. This in turn is highly detrimental to the autoxidation.

Although not essential, the autoxidation can be carried out under a slight positive pressure of oxygen.

The oxygen containing gas can be introduced into the reaction mixture using any suitable means known to those skilled in the art for the distribution and admixture of a gas into a liquid system. Illustratively, the gas can be sparged through a dip tube fitted with a fritted disc or other dispersing means known to those skilled in the art.

The metal phthalocyanine component of the catalyst combination that can be employed in the present invention is selected from the group consisting of copper, zinc, palladium, platinum, silver, and mercury. A particularly preferred phthalocyanine is copper phthalocyanine. The metal phthalocyanines are easily prepared using known techniques; see for example U.S. Pat. No. 2,954,405 (col. 3 lines 53–67) or else they are commercially available.

The metal phthalocyanine is advantageously employed in an amount of from about 0.001 percent by weight to about 1.0 percent by weight of the isopropylphenyl ester (I) and preferably from about 0.01 to about 0.6 percent.

Bulk autoxidation or autoxidation in a solvent diluent can be carried out in accordance with the present invention. Generally speaking, the starting material (I), if not a liquid at room temperature, is liquefied when exposed to the temperature ranges set forth above for carrying out the reaction.

In a preferred embodiment of the present invention the autoxidation is conducted in the presence of an inert aromatic solvent. The use of solvent reduces the occurrence of radical termination steps thereby increasing conversion rates. Accordingly, the quantity of solvent employed is not critical and can, conveniently, vary from about 20 percent by weight to about 200 percent by weight of the isopropylphenyl ester (I).

Any suitable inert aromatic solvent can be employed. A preferred group of solvents comprises benzene, t-butylbenzene, the halogenated benzenes such as chlorobenzene, o-dichlorobenzene, and the like. A particularly preferred solvent is chlorobenzene.

Particularly preferred combinations of catalyst and solvent in accordance with the present invention are (1) t-butyl hydroperoxide, copper phthalocyanine and chlorobenzene; and (2) t-butylhydroperoxide, dicumyl peroxide and chlorobenzene.

The isopropylphenyl esters (I) employed in the present process are defined hereinbefore and specifically excluded are those esters wherein the isopropyl group is substituted on the position ortho to the ester group. Illustrative examples of the isopropylphenyl esters used in the present process are p-(or meta)isopropylphenyl acetate, p-(or meta)isopropylphenyl propionate, p-(or meta) isopropylphenyl butyrate, p-(or meta)isoprophenyl valerate, p-(or metal)isopropylphenyl caproate, p-(or meta)isopropylphenyl heptylate, p-(or meta)isopropylphenyl caprylate, and the like; p-(or meta)isopropylphenyl benzoate, p-(or meta)isopropylphenyl naphthoate, p-(or meta)isopropylphenyl-p-toluate, p-(or meta)isopropylphenyl-p-ethylbenzoate, p-(or meta)isopropylphenyl-3,5-dimethyl-α-naphthoate, p-(or meta)isopropylphenyl-α-phenylacetate, p-(or meta)isopropylphenyl-β-phenylpropionate, and the like; illustrative examples of the esters (I) wherein n is 2 are 3,5-diisopropylphenyl acetate, 3,5-diisopropylphenyl benzoate, 3,5-diisopropylphenyl-p-toluate, 3,5-diisopropylphenyl-α-phenylacetate, and the like; bis(p-isopropylphenyl)terephthalate, bis(m-isopropylphenyl)terephthalate, bis(p-isopropylphenyl)2-methylterephthalate, bis(p-isopropylphenyl)isophthalate, bis(p-isopropylphenyl)phthalate, and the like; bis(p-isopropylphenyl)-carbonate, bis(m-isopropylphenyl)carbonate, bis(3,5-diisopropylphenyl)carbonate, and the like.

A preferred group of esters (I) is comprised of p-isopropylphenyl acetate, p-isopropylphenyl benzoate, bis(p-isopropylphenyl)carbonate, bis(m-isopropylphenyl)carbonate, bis(3,5-diisopropylphenyl)carbonate, and 3,5-diisopropylphenyl benzoate.

The carbonate esters are easily prepared using methods well known to those skilled in the art by the reaction of an excess of the appropriate isopropylphenol with phosgene, preferably in the ratio of 2:1 respectively, in the presence of a base to absorb the hydrogen chloride formed during the reaction; see for example, Synthetic Organic Chemistry by R.B. Wagner and H.D. Zook, page 483, 1953, John Wiley and Sons, New York, N.Y.

In an unexpected advantage to flow from the process of the present invention, the use of the bis(isopropylphenyl)carbonate compounds as starting materials provides a highly efficient and economic route to phenols in high purity, particularly hydroquinone. The use of the readily available and economically priced phosgene as the ester forming component with an isopropylphenol to form these bis(isopropylphenyl)carbonate starting materials is a novel and surprisingly advantageous technique.

The acid catalyzed rearrangement of hydroperoxyisopropylphenyl esters (II) to yield acetone and the corresponding hydroxyphenyl ester (III) with subsequent hydrolysis of the latter to the phenol (IV) are well known procedures in the art; see for example U.S. Pat. Nos. 2,799,695, 2,799,698, 2,799,715, and 3,028,410 cited supra whose disclosures in this respect are herein incorporated by reference.

The rearrangement of the hydroperoxide (II) to the phenolic compound (III) can be carried out on the reaction mixture as it is obtained directly from the autoxidation step. The pressure or absence of solvent is not a critical feature. While the hydroperoxide can be isolated, and, even purified if desired, it is not essential to the overall efficiency of the rearrangement and subsequent hydrolysis to the phenol. In a preferred embodiment, the hydroperoxide (II) is not isolated but rearranged in the reaction mixture in the presence of solvent.

Optionally, the relatively large proportion of starting isopropylphenyl ester (I), if easily distillable, can be removed from the crude autoxidation mixture prior to the rearrangement step. However, this is not essential as the isopropylphenyl esters (I) used in the present process are completely stable to the room temperature basic saponification conditions used to hydrolyze the ester grouping of the compounds (III), and, consequently, unreacted (I) can be recovered at the very end of the process after (IV) has been formed. A noteworthy characteristic of the hydroxyphenyl esters (III) is the ease with which the ester grouping can be hydrolyzed once the hydroxyl group is present on the aromatic ring. This will be discussed in detail hereinbelow. The precursor isopropylphenyl ester is not characterized by this same ease of hydrolyzability.

As noted above, the rearrangement of (II) is an acid catalyzed reaction and well known in the art and any of the methods described in the references cited supra can be employed in the present process. The acid catalyzed rearrangement is advantageously carried out within a temperature range of from about 0° C. to about 100° C., and preferably from about 20° C. to about 80° C. The time for the rearrangement to occur is not a critical feature and will vary depending on such factors at temperature, presence or absence of solvent, scale of reaction, etc. Generally speaking, the time will vary from a matter of minutes (about 15 minutes) to a number of hours (about 4 hours). Acid catalysts such as sulfuric, hydrochloric or p-toluenesulfonic acids, boron trifluoride etherate, or the like are used, advantageously in an amount of from about 0.01 weight percent to about 5.0 weight percent of compound (II) and preferably from about 0.1 weight percent to about 1.0 weight percent. A preferred group comprises boron trifluoride etherate and sulfuric acid. A most preferred catalyst is boron trifluoride etherate.

The rearrangement can proceed in high yield (>95%) to acetone and the hydroxyphenyl ester compound (III). The impurities present are very minor amounts of the acetophenone derivative, which arises from the rearrangement of (II), and an ispropenylphenyl ester. The former impurity is formed in the autoxidation step while the latter arises from the dehydration, during the rearrangement, of the hydroxyisopropylphenyl ester side product which is also formed in the autoxidation step as a minor impurity.

The bisphenol carbonates of formula (III) wherein R is the hydroxyphenyloxy radical [derived from (Ia)], find particular utility in the preparation of polycarbonate polymers well known to those skilled in the art.

When it becomes desirable to isolate the hydroxyphenyl esters (III) formed from the rearrangement, as in the case of the bisphenol carbonates referred to hereinabove, a non-solvent for the hydroxyphenyl ester is simply added to the crude reaction mixture. For example, the addition of solvents such as hexane, petroleum ether, benzene, methylene chloride, and the like will cause the selective precipitation of the dihydroxyphenyl ester from any monohydroxyl compound and particularly the bisphenol carbonates as crystalline solids.

The hydrolysis of the hydroxyphenyl esters (III) to the corresponding phenols (IV) is readily accomplished using either acid or base catalyzed hydrolysis. However, base catalyzed hydrolysis is preferred and any of the techniques set forth in the patents cited supra whose disclosures have been incorporated herein can be used in the present process.

A preferred method for the hydrolysis of the crude rearrangement mixture comprises simply shaking the reaction solution with dilute aqueous alkali metal hydroxide solution (e.g. 5-20 wt. percent sodium hydroxide solution) at room temperature. Preferably, the hydrolysis is carried out under nitrogen, or else, in the presence of a minor amount of an antioxidant such as sodium sulfite to inhibit possible oxidation of the formed phenols (IV) which are somewhat susceptible to air oxidation in basic solution.

The phenols can be isolated using any convenient separation methods known to those skilled in the art. The alkali metal hydroxide is either acidified by dilute hydrochloric acid or neutralized by the addition of carbon dioxide, whereafter the product can be either extracted from the solution or will crystallize therefrom.

The overall process according to the present invention provides in-hand yields of phenols, and hydroquinone in particular, at conversion levels and rates of conversion based on starting isopropylphenyl ester, heretofore not obtainable.

The new process offers high conversions in the autoxidation step at high selectivities (90–95%) which gives rise to overall yields of compounds like hydroquinone as high, or higher, than 90%. Furthermore, the dihydric phenols, which are recognized in the art as being difficult to obtain in a high state of purity, are obtained from the present process in excellent purity.

The dihydric phenols produced in accordance with the present invention such as hydroquinone, resorcinol, and the like are used as intermediates in the preparation of other compositions, for example in the preparation of various polymers such as poly(1,4-phenylene adipate), poly(1,3-phenylene adipate), poly(1,4-phenylene phosphonate), poly(1,4-phenylene sebacate), and the like.

Hydroquinone is particularly useful in photographic developer formulations and also as an oxidation inhibitor.

The following examples describe the manner and process of making and using the invention and set forth the best mode contemplated by the inventor of carrying out the invention but are not to be construed as limiting.

ANALYTICAL METHODS

The analyses of the autioxidation reactions exemplified below and the products obtained therefrom were performed either by (A) the technique of high pressure liquid chromatography (HPLC) or (B) by the nuclear magnetic resonance (NMR) measurements which methods are described generally below. The latter technique was preferably used in monitoring the progress of the autoxidation while the former was preferably used in determining product identity and concentration.

(A) HPLC analysis was preformed in a Waters Model 6000 Machine with dual detectors (Model 202/R401), Waters Associates, Milford, Mass., 01757, by passing an aliquot of the reaction solution through a u-Porasil column (4 mm ID×30 cm. length) operating at a flow rate of 1.2–1.5 ml./min. and using a solvent mixture of acetonitrile 7.5% by volume and ethylene dichloride 92.5% by volume at room temperature.

(B) NMR analysis was performed in a Varian T-60 spectrometer using internal TMS as standard in carbon tetrachloride as solvent on an aliquot of the reaction mixture by measuring the proton resonance. The singlet peak at $\delta 1.52$ for the protons of the two methyl groups of the hydroperoxyisopropyl group was compared to the doublet resonance at $\delta 1.23$ for the methyl protons of the unreacted isopropyl group.

EXAMPLE 1

A three-necked round bottom flask equipped with an oxygen bubbler, a thermometer fitted with a thermometer regulator, magnetic stirrer, and a condenser was charged with 93.06 g. (0.523 mole) of p-isopropylphenyl acetate, 0.40 g. (0.43 wt. % based on the acetate) of copper phthalocyanine, and a trace amount (2 drops or about 0.1 g.) of t-butyl peroxide. Oxygen was bubbled into the solution at a rapid rate (flow rate 25 ml./min.) while the solution was heated for 30 minutes at 125°–130° C. and thereafter at 115° C. for 5 hours.

The progress of the autoxidation to p-hydroperoxyisopropylphenyl acetate was monitored using the NMR technique described above and showed the following progression of the conversion: at 60 minutes, 7.5%; at 120 minutes, 18.8%; at 180 minutes, 23.5%; and at 300 minutes, 28.8%. The rate of conversion was 8 mole%/hour and there was no induction period prior to the beginning of the autoxidation. HPLC analysis showed a 91% content (selectivity) in the oxidation product mixture of p-hydroperoxyisopropylphenyl acetate.

EXAMPLE 2

A round bottomed flask equipped according to Example 1 was charged with 10.2 g. (0.057 mole) of p-isopropylphenyl acetate, 0.10 g. (1.0 wt. %) of t-butyl hydroperoxide, 0.02 g. (0.2 wt. %) of copper phthalocyanine (supplied by Eastman Chemicals, Rochester, New York), and 5.0 g. (49 wt. %) of chlorobenzene. Oxygen was bubbled into the stirred solution (flow rate 20 ml./min.) for a 10 minute period at a solution temperature of 120°–125° C. and then for 4 hours at 115°±3° C. The conversion rate was monitored by the NMR technique and the actual content (selectivity) of the desired p-hydroperoxyisopropylphenyl acetate was concurrently measured (where it is noted below) and the results are shown in the following tabulation.

| Time of Reaction (minutes) | Mole % Conversion to Hydroperoxide | % Content of Desired Hydroperoxide |
|---|---|---|
| 30 | 5.6 | — |
| 60 | 11.1 | — |
| 90 | 19.8 | — |
| 120 | 26.7 | 93.4 |
| 150 | 37.6 | 91.8 |
| 180 | 43.2 | 89.8 |
| 210 | 46.5 | — |
| 240 | 46.7 | 88.9 |

Based on the above mole % conversion, the actual rate of conversion was 16 mole %/hour with little or no induction period.

EXAMPLE 3

A round bottomed flask equipped according to Example 1 was charged with 34.45 g. (0.144 mole) of p-isopropylphenyl benzoate, 0.17 g. (0.49 wt. %) of di-t-butyl peroxide, 0.20 g. (0.58 wt. %) copper phthalocyanine, and 10 ml. of benzene. Oxygen was bubbled into the solution (flow rate 20 ml./min.) for about 20 minutes at a solution temperature of 120°–125° C. and thereafter for 10 hours at 115° C.±2° C. The progress of the autoxidation was followed by NMR analysis to determine the conversion of the starting benzoate to the desired p-hydroperoxyisopropylphenyl benzoate. After 180 minutes the molar conversion was 11.3%; 300 minutes, 21.0%; 480 minutes, 27.7%; finally at 600 minutes, 36.6%. The rate of conversion was 4.4 mole %/hour and the selectivity of the desired product determined by HPLC was 87.4%. The autoxidation initiated without an induction period.

The reaction solution was diluted with 100 ml. of benzene and filtered to recover the copper phthalocyanine, wt., 0.21 g. To the filtrate there were added 6 drops of boron trifluoride etherate and this solution stirred for 4 hours. The temperature was initially room temperature (circa 20° C.) but increased to 60° C. and returned to room temperature over the 4 hour period. A precipitate of p-hydroxyphenyl benzoate was collected, wt., 4.89 g., m.p. 158°–161° C. To the mother liquor, 100 ml. of carbon tetrachloride was added causing the precipitation of additional p-hydroxyphenyl benzoate, wt., 5.66 g., m.p. 156°–162° C. The total yield of 10.55 g. of p-hydroxyphenyl benzoate was equivalent to a 93.4% yield.

EXAMPLE 4

A round bottomed flask equipped according to Example 1 was charged with 15.0 g. (0.0625 mole) of p-isopropylphenyl benzoate, 0.15 g. (1.0 wt. %) of t-butyl hydroperoxide, 0.03 g. (0.2 wt. %) of copper phthalocyanine, and 3.0 g. (20 wt. %) of chlorobenzene. Oxygen was bubbled into the solution (flow rate 20 ml./min.) for 5 minutes at a solution temperature of 125°–130° C. and thereafter for 4 hours at 115°±3° C. The progress of the autoxidation was followed by NMR analysis to determine the conversion of the starting material to p-hydroperoxyisopropylphenyl benzoate. After 30 minutes the molar conversion was 2.1%; 60 minutes, 9.6%; 120 minutes, 20.5%; 180 minutes, 28.5%; finally at 240 minutes, 39.4%. The rate of conversion was 9.8 mole %/hour and the selectivity of the desired product determined by HPLC was 94.5%. There was no induction period.

EXAMPLE 5 p-Isopropylphenol (200.5 g., 1.474 moles) was dissolved with 1.5 liters of 2.2 N sodium hydroxide solution. This solution was charged to a 3 liter three-necked round bottom flask equipped with a mechanical stirrer and an addition funnel. Triethylamine (2.0 g.) was added to the solution while it was cooled to 0° C. by means of an ice bath. To the solution there was added over a 2 hour period, a solution of 150 g. (1.52 moles) of phosgene in 200 ml. of toluene. The solution was then allowed to warm up to room temperature by continued stirring for 2 hours.

The reaction solution was extracted with 3×130 ml. portions of ether and the combined ether fractions dried over magnesium sulfate. Ether and volatile material was removed in vacuo to provide 223 g. (approximately 100% yield) of di(p-cumyl)carbonate or bis(p-isopropylphenyl) carbonate. It was recrystallized twice from 300 ml. of methanol each time and yielded 205.1 g. (93.4%) of needles of pure di(p-cumyl)carbonate which has the following properties: m.p. 59°–60° C.; infrared absorption spectrum (CHCl$_3$) (cm$^{-1}$), 3040, 2970, 1755, 1605, 1508, 1460, 1420, 1385, 1365, 1235, 1190, 1163, 1200, 1057, 1020, 1010, 889, and 829; NMR(CDCl$_3$) δ7.15 (s,8), 2.89 (m,2), 1.22 (d,12); HPLC retention time of 2.45 minutes, u-Porasil column (4 mm. ID×30 cm. length); solvent: 9.75% acetonitrile+90.25% ethylene dichloride; and the following elemental analysis Calcd. for C$_{19}$H$_{22}$O$_3$: C, 76.48%; H, 7.43%; Found: C, 76.37%; H, 7.47%.

The following process although not in accordance with the present invention was employed to obtain di(p-hydroperoxyisopropylphenyl)carbonate.

A round bottomed flask equipped according to Example 1 was charged with 46.10 g. (0.155 mole) of di(p-cumyl) carbonate, 0.25 g. (0.54 wt. %) of di-t-butyl peroxide and 6 ml. of benzene. Oxygen was bubbled into the solution (flow rate about 15 ml./min.) for 15 minutes at a solution temperature of 120°–125° C. and thereafter for 7 hours at 115° C. NMR analysis was used to observe the following molar hydroperoxide formation: after 120 minutes, 8.9%, 240 minutes, 18.6%; 360 minutes, 26.1%; finally at 420 minutes, 29.6%. The rate of conversion was 4.5 mole %/hour. HPLC analysis showed the following selectivity: di(p-hydroperoxyisopropylphenyl)carbonate, 11.8%; (p-hydroperoxyisopropylphenyl)cumyl carbonate, 85.0%; (p-hydroxyisopropylphenyl)cumyl carbonate, 3.2%.

Recrystallization of a sample of the di(p-hydroperoxyisopropylphenyl)carbonate from p-dioxane provided crystalline needles, m.p. 122°–124° C; HPLC retention time of 4.79 minutes ($_u$-Porasil column 4 mm. ID×30 cm. length, solvent 9.75% acetonitrile and 90.25% ethylene chloride), and having the following elemental analysis Calcd. for C$_{19}$H$_{22}$O$_7$: C, 62.97%; H, 6.12%; Found: C, 62.80%; H, 6.15%.

The following process was in accordance with the present invention and demonstrates the much higher selectivity in comparison to the experiment above.

A round bottom flask equipped according to Example 1 was charged with 36.77 g. (0.123 mole) of di(p-cumyl) carbonate prepared above, 0.22 g. (0.58 wt. %) of copper phthalocyanine, 0.12 g. (0.33 wt. %) of di-t-butyl peroxide, and 10 ml. of benzene. Oxygen was bubbled into the solution (flow rate of 40 ml./min.) for 20 minutes at a solution temperature of 125°–130° C. and thereafter for another eight hours and 40 minutes. NMR and HPLC were used to monitor the progress of the reaction and NMR showed the following molar hydroperoxide formation: after 60 minutes, 3.8%; 120 minutes, 6.4%; 180 minutes, 11.7%; 300 minutes, 22.8% 360 minutes, 26.1%; finally 540 minutes, 39.1%. The rate of conversion was 4.2 mole %/hour. HPLC showed the distribution of the 3 major products to be mono-hydroperoxide (p-hydroperoxyisopropylphenyl cumyl carbonate) 74.01%; mono-alcohol (p-hydroxyisopropylphenyl cumyl carbonate) 6.61%; and di-hydroperoxide[di(p-hydroperoxyisopropylphenyl)carbonate] 19.30%. There was no induction period.

The reaction mixture was diluted with 150 ml. of benzene and filtered to recover 0.21 g. (95.5% recovery) of copper phthalocyanine. The solution was stirred with 0.1 g. of boron trifluoride etherate over a period of 2.25 hours during which time the solution was at 35°–60° C. from its own exotherm. Evaporation of the benzene yielded 39.18 g. of crude solid product.

The solid residue was triturated with 200 ml. of hexane which upon evaporation afforded 14.10 g. of crystalline solid which contained about 13 g. of starting di(p-cumyl)carbonate while the balance of 1.1 g. consisted of a 50/50 mixture of p-cumyl (p-isopropenylphenyl)carbonate and p-cumyl(p-hydroxyphenyl)carbonate.

The hexane insoluble solid portion of 19.50 g. consisted largely of the mixture of p-cumyl(p-hydroxyphenyl)carbonate and bis(p-hydroxyphenyl)carbonate in the approximate ratio of 80%/20% respectively. The isolation of the latter bisphenol carbonate was effected by triturating the solid with 2×50 ml. portions of methylene chloride. The undissolved portion, 6.6 g. (m.p. 150°–167° C.) was recrystallized from 20 ml. of 1,4-dioxane to yield 2.87 g. of needles of pure bis(p-hydroxyphenyl)carbonate, m.p. 188°–189° C.; NMR (acetone -d$_6$); δ7.00(q,8), 3.01(s,2); HPLC retention time of 6.89 minutes (u-Porasil column 4 mm. ID×30 cm. length, solvent 9.75% acetonitrile+90.25% ethylene dichloride); and the following elemental analysis:

Calcd. for C$_{13}$H$_{10}$O$_5$: C, 63.42%; H, 4.09%; Found: C, 63.28%; H, 4.06%.

The monophenol or p-cumyl(p-hydroxyphenyl)carbonate was recrystallized from either benzene or carbon tetrachloride, m.p. 126°–128° C.; infrared absorption spectrum (cm$^{-1}$): 3580, 3420, 3015, 2978, 1755, 1580, 1495, 1435, 1230, 1170, 1088, 1045, 1001, 878, 819; NMR (acetone -$d_6$): δ7.13 (m,4), 6.87 (q,4), 2.94 (m,1), 1.13 (d,6), 8.40 (s,1); HPLC retention time of 3.29 minutes (same conditions as above); and the following elemental analysis Calcd. for $C_{16}H_{16}O_4$: C, 70.57%; H, 5.92%; Found: C, 70.47%; H, 5.87%.

EXAMPLE 6

A round bottom flask equipped according to Example 1 was charged with 14.90 g. (0.05 mole) of di(p-cumyl) carbonate, 0.03 g. (0.20 wt. %) of copper phthalocyanine, 0.15 g. (1.0 wt. %) of t-butyl hydroperoxide, and 5 g. (33.6 wt. %) of chlorobenzene. Oxygen was bubbled into the solution (flow rate about 20 ml./min.) for 5 minutes at a solution temperature of 125°–130° C. and thereafter for 2.75 hours at 115°±3° C. NMR showed the following molar hydroperoxide formation: after 0.5 hour, 5.3%; 1.0 hour, 9.5%; 1.5 hours, 16.3%; 2 hours, 24.3%; 2.5 hours, 31.8%; 2.75 hours, 33.3%. The rate of conversion was 12 mole %/hour. There was no induction period. HPLC showed the following selectivity.

(p-hydroperoxyisopropylphenyl)cumyl carbonate 85.7%
(p-hydroxyisopropylphenyl)cumyl carbonate 6.0%
di(p-hydroperoxyisopropylphenyl)carbonate 6.0%
(p-hydroxyphenyl)cumyl carbonate 1.5%.

EXAMPLE 7

A round bottom flask equipped according to Example 1 was charged with 28.50 g. (0.16 mole) of m-isopropylphenyl acetate, 0.6 g. (0.21 wt. %) of copper phthalocyanine, and 0.30 g. (1.1 wt. %) of t-butyl hydroperoxide. Oxygen was bubbled into the stirred solution (flow rate 20 ml./min.) for 15 minutes at a solution temperature of 125°–130° C. and thereafter for 6.5 hours at 115°±3° C.

NMR monitoring showed the following molar hydroperoxide formation: after 60 minutes, 3.63%; 120 minutes, 10.0%; 180 minutes, 13.1%; 270 minutes, 20.5%, 360 minutes, 23.0%; finally at 390 minutes, 24.9%. The rate of conversion was 4.8 mole %/hour. There was no induction period. HPLC analysis showed the following selectivity.

m-hydroperoxyisopropylphenyl acetate 95.8%
m-acetoxyacetophenone 1.59%
m-hydroxyisopropylphenyl acetate 6.32%.

EXAMPLE 8 m-Isopropylphenol, 36.06 g. (0.265 mole) was dissolved in dilute excess sodium hydroxide solution. To this solution was added 1 g. of triethylamine and during rapid stirring there was added dropwise a solution of 28.4 g. (0.14 mole) of terephthaloyl dichloride dissolved in 150 ml. of methylene dichloride. The reaction solution was cooled until the addition was completed.

The organic layer was separated and the aqueous layer extracted with 2×100 ml. of methylene chloride and combined with the organic layer. The solution was evaporated in vacuo and yielded 51.18 g. of product. Recrystallization from methanol yielded 51.01 g. (95.4%) of di(m-isopropylphenyl)terephthalate, m.p. 79°–81° C.; NMR (CDCl$_3$): δ8.32 (s,4), 6.90–7.40 (m,8), 2.98 (m,1), 1.31 (d,12).

Into a round bottom flask equipped according to Example 1 there was added 41.0 g. (0.10 mole of the di(m-isopropylphenyl)terephthalate prepared above, 0.4 g. (1 wt. %) of t-butyl hydroperoxide, 0.08 g. (0.2 wt. %) of copper phthalocyanine, and 10 ml. of benzene. Oxygen was bubbled into the solution (flow rate 20 ml./min.) at a temperature of 115°±3° C. for 10 hours and 15 minutes. NMR analysis showed that conversion to hydroperoxide was 11.6 mole % after 4 hours and 35 mole % when the reaction was stopped after 10 hours.

The hydroperoxide consisted of a mixture of predominantly m-isopropylphenyl-m-hydroperoxyisopropylphenyl terephthalate and the di(m-hydroperoxyisopropylphenyl) terephthalate. No attempt was made to separate the compounds.

EXAMPLE 9

The following process although not in accordance with the present invention was employed to obtain 3,5-di(hydroperoxyisopropyl)phenyl benzoate.

A round bottom flask equipped according to Example 1 was charged with 9.1 g. (0.0322 mole) of 3,5-diisopropylphenyl benzoate, 0.09 g. (1.0 wt. %) of di-t-butyl peroxide, and 15 g. of chlorobenzene. Oxygen was bubbled into the solution (flow rate about 15 ml./min.) for 10 minutes at a solution temperature of 120°–125° C. and thereafter for 7 hours at 115° C. NMR showed the following molar hydroperoxide formation: after 1.5 hours, 3%; 4 hours, 14.1%; 5 hours, 19.3%; and 7 hours, 23.3%. The reaction temperature was reduced to 90°–95° C. and the reaction was allowed to continue overnight at that temperature and at the oxygen flow set forth above.

After a 16 hour period at the 90°–95° C. temperature the percent molar hydroperoxide conversion was 36.7% and the reaction stopped at a 38.8% conversion.

HPLC showed the following selectivity distribution.
3-hydroperoxyisopropyl-5-isopropylphenyl benzoate 56.5%
3,5-di(hydroperoxyisopropyl)phenyl benzoate 37.2%
3-hydroxyisopropyl-5-isopropylphenyl benzoate 6.2%.

The rate of conversion was 4.6mole %/hour measured over the reaction period from the second to the fifth hour.

The reaction product mixture was stirred with 75 ml. of pet ether which caused the precipitation of 2.14 g. of crystalline residue; m.p. 105°–108° and consisted of 60% by weight of the dihydroperoxy product and 40% of the monohydroperoxide. Recrystallization of the precipitate from chloroform provided the pure 3,5-di(hydroperoxyisopropyl) phenyl benzoate; m.p. 122°–124° C., NMR (CDCl$_3$): δ8.48 (s,2), 8.16 (m,2), 7.45 (m,4), 7.16 (d,2), 1.62 (s, 12); and the following elemental analysis Calcd. for $C_{19}H_{22}O_6$: C, 65.88%; H, 6.40%; Found: C, 65.68%; H, 6.51%.

A 0.62 g. sample of the dihydroperoxide product was rearranged in 10 ml. of benzene with 2 drops of boron trifluoride etherate at 60° C. The reaction was instantaneous with the immediate formation of the crystalline 3,5-dihydroxyphenyl benzoate, 0.31 g. (75% yield), m.p. 195°–196° C.

Shaking the dihydroxyphenyl benzoate in dilute aqueous caustic solution provides 1,3,5-trihydroxybenzene (phloroglucinol).

EXAMPLE 10

Using the procedure and ingredients set forth in Example 5 for the preparation of bis(p-isopropylphenyl)

carbonate except that the p-isopropylphenol was replaced by an equivalent amount of 3,5-diisopropylphenol, there was prepared bis(3,5-diisopropylphenyl)carbonate in a crude yield of 100%. Recrystallization of the product from methanol provided a 77.8% pure yield; m.p. 53°–55° C.; infrared absorption spectrum (CHCl$_3$) (cm$^{-1}$) 2965, 2930, 2875, 1780, 1615, 1591, 1468, 1460, 1442, 1226, 1160, 1127, 1000, 940, and 670; NMR (CCl$_4$) at δ6.92 (s,6), δ2.91 (m,4), δ1.30 (d,24); elemental analysis, Calcd. for $C_{25}H_{34}O_3$: C, 78.49%; H, 8.96%; Found: C, 78.26%; H, 8.91%.

The following process although not in accordance with the present invention was employed to obtain bis(3,5-dihydroperoxyisopropylphenyl)carbonate.

A round bottom flask equipped according to Example 1 was charged with 19.1 g. (0.05 mole) of the bis(3,5-diisopropylphenyl)carbonate prepared above, 0.20 g. (1 wt.%) of t-butyl hydroperoxide and 20 g. (approximately 100% w/w) of chlorobenzene. Oxygen was bubbled into the solution (flow rate about 15 ml./min.) at a solution temperature of 115±3° C. and the progress of the autoxidation monitored by NMR. After 3 hours the percent molar conversion was 8.1%; 5 hours, 17.5%; and 6.25 hours, 25%. The reaction was continued overnight (for a 14 hour period) at 100° C. The final conversion was 62.7%. HPLC analysis showed the presence of five major hydroperoxide products.

The reaction solution was diluted with 150 ml. of chlorobenzene and after standing overnight, 0.75 g. of precipitated bis(3,5-dihydroperoxyisopropylphenyl)carbonate was collected, m.p. 119°–130° C. Recrystallization from chloroform provided pure material, m.p. 135°–138° C., elemental analysis, Calcd. for $C_{25}H_{34}O_{11}$: C, 58.81%; H, 6.71%; Found: C, 57.89%; H, 6.98%.

The remaining chlorobenzene solution was treated with 6 drops (about 0.1 g.) of boron trifluoride etherate at a temperature of 30°–40° C. An exothermic reaction ensued and the temperature was controlled to a range of 50°–80° C. by a water bath over a 2 hour period during stirring.

The reaction solution was added to 100 ml. of ether and this solution shaken with 3×25 ml. portions of 15 percent aqueous sodium hydroxide. The ether layer upon evaporation yielded 4.06 g. of starting carbonate material. The aqueous layer was acidified and extracted with ether. HPLC analysis revealed two major components corresponding to 3,5-dihydroxyisopropylbenzene ($R_T$=3.75 minutes) and 1,3,5-trihydroxybenzene ($R_T$=9.40 minutes) on a u-Porasil column (4 mm. ID×30 cm. length) operating at a flow rate of 1.5 ml./min. in a solvent mixture of 16% by wt. acetonitrile in ethylene dichloride.

The two products were separated by column chromatography using a dry packed silica gel column eluted with ether. When 3.50 g. of the mixture was diluted in 10 ml. of ether and eluted through a 2 cm.×40 cm. column there was obtained as separated products 1.52 g. of the 3,5-dihydroxyisopropylbenzene, 0.49 g. of 1,3,5-trihydroxybenzene, and 0.31 g. of unidentified material.

EXAMPLE 11

A round bottomed flask equipped according to Example 1 was charged with 17.8 g. (0.1 mole) of p-isopropylphenyl acetate, 0.09 g. (0.5 wt. %) of t-butyl hydroperoxide, and 0.15 g. of di-t-butyl peroxide (0.8 wt. %). Oxygen was bubbled into the solution (flow rate 8–10 ml./min.) at a solution temperature of 115°±3° C. The temperature control apparatus allowed the initial temperature to rise to about 120° C. for a few minutes prior to settling on the controlled value. The mole percent conversion was determined by NMR and product selectivity by HPLC. At the end of a 4 hour reaction period the mole % conversion was 22.5% at a conversion rate of 5.62 mole % per hour with no induction period. The product distribution was found to be: 96.9% p-hydroperoxyisopropylphenyl acetate, and 3.1% p-hydroxyisopropylphenyl acetate.

EXAMPLE 12

A round bottomed flask equipped according to Example 1 was charged with 17.8 g. (0.1 mole) of p-isopropylphenyl acetate, 0.27 g. (1.5 wt. %) of dicumyl peroxide, 0.153 g. (0.86 wt. %) of cumyl hydroperoxide, and 6 g. of chlorobenzene. Oxygen was bubbled into the solution (flow rate 10 ml./min.) at a solution temperature of 115°±3° C. (See Example 11 for explanation of an initial temperature rise to 120° C.). At the end of a 5 hour reaction period the mole % conversion was 33.3% at a rate of 7.48 mole % per hour with no induction period. The selectivity was found to be: 93.4% p-hydroperoxyisopropylphenyl acetate, and 6.6% p-hydroxyisopropylphenyl acetate.

EXAMPLE 13

A round bottomed flask equipped according to Example 1 was charged with 17.8 g. (0.1 mole) of p-isopropylphenyl acetate, 0.27 g. (1.5 wt. %) of dicumyl peroxide, 0.10 g. (0.56 wt. %) of t-butyl hydroperoxide, and 6.0 g. of chlorobenzene. Oxygen was bubbled into the solution (flow rate 10 ml./min.) at a solution temperature of 115°±3° C. (See Example 11 for explanation of an initial temperature rise to 120° C.). At the end of a 3.5 hour reaction period the mole % conversion was 32.7% at a rate of 10.1 mole % per hour with no induction period. The selectivity was found to be: 93.5% p-hydroperoxyisopropylphenyl acetate, and 6.5% p-hydroxyisopropylphenyl acetate.

EXAMPLE 14

A round bottomed flask equipped according to Example 1 was charged with 17.8 g. (0.1 mole) of p-isopropylphenyl acetate, 0.15 g. (0.84 wt. %) of di-t-butyl peroxide, 0.15 g. (0.84 wt. %) of cumyl hydroperoxide, and 6.0 g. of chlorobenzene. Oxygen was bubbled into the solution (flow rate 10 ml./min.) at a solution temperature of 115°±3° C. (See Example 11 for explanation of an initial temperature rise to 120° C.). At the end of a 6.0 hour reaction period the mole % conversion was 28.7% at a rate of 5.26 mole % per hour with no induction period. The selectivity was found to be: 95.8% p-hydroperoxyisopropylphenyl acetate, and 4.2% p-hydroxyisopropylphenyl acetate.

EXAMPLE 15

The following experiment not in accordance with the present invention illustrates how a low temperature free radical initiating reagent like azo-bis-isobutyronitrile will not give the same high conversions with high product selectivity as does the present invention.

A round bottomed flask equipped according to Example 1 was charged with 17.8 g. (0.1 mole) of p-isopropylphenyl acetate, 0.10 g. (0.56 wt. %) of t-butyl hydroperoxide, 0.17 g. (0.96 wt. %) of azo-bis-isobutyronitrile, and 9 g. of chlorobenzene. Oxygen was bubbled into the solution (flow rate 10 ml./min.) at a solution temperature of 85°±3° C. After 1.5 hours of reaction the NMR analysis showed the complete disappearance of the azo-bis-isobutyronitrile and substantial decomposition of hydroperoxide. After a 2 hour reaction period the mole % conversion was 19.8% at a rate of 9.90 mole % per hour. The selectivity was found to be low for desired product at 78.6% p-hydroperoxyisopropylphenyl acetate, 16.1% p-hydroxyisopropylphenyl acetate, and 5.3% p-acetoxyacetophenone.

Repetition of the autoxidation at a lower temperature (70°±3° C.) in an endeavour to lower hydroperoxide decomposition lead to an observed increase of product selectivity of 89.1%. However, the rate over a 4 hour reaction period was only 3.18 mole % per hour and the mole % conversion was only 12.7%.

EXAMPLE 16

The following experiment not in accordance with the present invention illustrates how when only one of the catalyst components is employed but at a higher concentration which is approximately equal to the sum total for the two catalysts in accordance with the invention that the rate of the reaction is lowered and a long induction period results.

A round bottomed flask equipped according to Example 1 was charged with 17.8 g. (0.1 mole) of p-isopropylphenyl acetate and 0.36 g. (2 wt. % but, more importantly, when calculated on a mole % basis it is 2.47 mole % which is more than twice as much as the concentrations used in comparative examples) of di-t-butyl peroxide. Oxygen was bubbled into the solution (flow rate 10 ml./min.) at a solution temperature of 115°±3° C. After a 6.5 hour reaction period the mole % conversion was 23.0 mole % at a rate of only 3.73 mole % per hour. There was an induction period of about 1 hour before inception of the autoxidation. The selectivity was found to be: 94.5% p-hydroperoxyisopropylphenyl acetate and 5.5% p-hydroxyisopropylphenyl acetate.

EXAMPLE 17

The following experiments not in accordance with the present invention illustrate how three known autoxidizing agents will not give the same high conversion rates or induction free reactions in accordance with the present invention.

A round bottomed flask equipped according to Example 1 was charged with 17.8 g. (0.1 mole) of p-isopropylphenyl acetate, and 0.15 g. (0.84 wt. %) of cumyl hydroperoxide. Oxygen was bubbled into the solution (flow rate 8–10 ml./min.) at a solution temperature of 115°±3° C. After an 8.0 hour reaction period the mole % conversion was only 20.2% at a rate of only 2.53 mole % per hour. There was almost a 2 hour induction period before the autoxidation began. The selectivity was 96.8% p-hydroperoxyisopropylphenyl acetate and 3.2% p-hydroxyisopropylphenyl acetate.

The experiment was repeated using t-butyl hydroperoxide in the same concentration. After a 7 hour reaction period the conversion was only 13 mole % at a rate of 1.86 mole % per hour with an induction period just slightly over 1.5 hours. The selectivity was 97.7% p-hydroperoxyisopropylphenyl acetate and 2.3% p-hydroxyisopropylphenyl acetate.

When the same autoxidation was performed using 30% hydrogen peroxide in the same concentration after 7 hours the conversion was only 2.6 mole % at the rate of 0.37 mole % per hour and with a 3.75 hour induction period. Selectivity was not determined.

I claim:
1. A dihydroperoxide having the formula

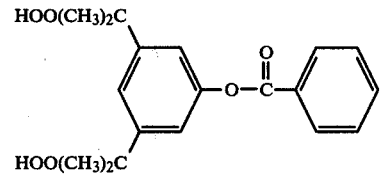

* * * * *